United States Patent [19]

Van Gompel et al.

[11] Patent Number: 4,938,757

[45] Date of Patent: Jul. 3, 1990

[54] DISPOSABLE TRAINING PANT OR INCONTINENCE GARMENT

[75] Inventors: Paul T. Van Gompel, Hortonville; Jody D. Suprise; Leona G. Boland, both of Neenah; Georgia L. Zehner, Larsen, all of Wis.

[73] Assignee: Kimberly-Clark Corporation, Neenah, Wis.

[21] Appl. No.: 372,414

[22] Filed: Jun. 27, 1989

Related U.S. Application Data

[63] Continuation of Ser. No. 133,758, Dec. 16, 1987, abandoned.

[51] Int. Cl.⁵ .............................................. A61F 13/16
[52] U.S. Cl. .................................. 604/396; 604/385.2
[58] Field of Search ............................. 604/396, 385.2

[56] References Cited

U.S. PATENT DOCUMENTS

| | | |
|---|---|---|
| 2,102,359 | 12/1937 | Frieman . |
| 2,252,019 | 8/1941 | Meinecke et al. . |
| 2,397,641 | 4/1946 | Blair . |
| 2,435,945 | 2/1948 | Redmond . |
| 2,538,596 | 1/1951 | Sheridan . |
| 3,087,495 | 4/1963 | Hort . |
| 3,098,484 | 7/1963 | Younger . |
| 3,142,301 | 7/1964 | Erteszek . |
| 3,368,563 | 2/1968 | Scheier . |
| 3,386,446 | 6/1968 | Sloan . |
| 3,397,696 | 8/1968 | Rickard . |
| 3,530,859 | 9/1970 | Heimowitz ..................... 604/386 |
| 3,613,687 | 10/1971 | Kennedy . |
| 3,687,141 | 8/1972 | Matsuda . |
| 3,768,481 | 10/1973 | Shibata . |
| 3,882,871 | 5/1975 | Taniguchi . |
| 4,031,568 | 6/1977 | Huff . |
| 4,205,679 | 6/1980 | Repke et al. . |
| 4,355,425 | 10/1982 | Jones et al. . |
| 4,425,127 | 1/1984 | Suzuki et al. . |
| 4,425,128 | 1/1984 | Motomura . |
| 4,427,408 | 1/1984 | Karami et al. . |
| 4,522,853 | 6/1985 | Szonn et al. . |
| 4,534,769 | 8/1985 | De Jonckhiere et al. . |
| 4,610,680 | 9/1986 | La Fleur . |
| 4,619,649 | 10/1986 | Roberts . |
| 4,642,819 | 2/1987 | Ales et al. . |
| 4,655,760 | 4/1987 | Morman et al. . |
| 4,690,681 | 9/1987 | Haunschild et al. . |
| 4,695,279 | 9/1987 | Steer . |
| 4,704,114 | 11/1987 | Wilson et al. . |

FOREIGN PATENT DOCUMENTS 1520740 8/1978 United Kingdom .

Primary Examiner—C. Fred Rosenbaum
Assistant Examiner—Sharon Rose
Attorney, Agent, or Firm—Douglas L. Miller

[57] ABSTRACT

A disposable pant-like garment for absorbing human discharge comprises an absorbent assembly including a liquid impervious outer cover, a liquid pervious liner, and an absorbent medium therebetween. A pair of stretchable side panels are joined to the absorbent assembly to form a waist opening and a pair of leg openings, and an intermediate portion of each stretchable side panel is generally peripherally disposed about a respective leg opening. The stretchable side panels provide generally inwardly directed force vectors against a wearer to maintain the garment snugly against the wearer's body and the absorbent assembly snugly in place against the crotch area both before and after a discharge.

58 Claims, 10 Drawing Sheets

DISPOSABLE TRAINING PANT OR INCONTINENCE GARMENT

This is a continuation application of application Ser. No. 07/133,758, filed on Dec. 16, 1987, now abandoned.

BACKGROUND OF THE INVENTION

This invention pertains to an absorbent article, and more particularly to an absorbent article for use as a child's training pant, adult incontinence garment, baby diaper and the like.

Currently, disposable absorbent articles find widespread use for infant care and adult incontinence care, and have generally replaced the use of reusable cloth absorbent articles, such as cloth diapers. The typical disposable absorbent article is a three-layered composite structure comprising a liquid-permeable bodyside liner, a liquid-impermeable outer cover and an absorbent batt disposed between the bodyside liner and the outer cover. Materials now in general use for the three principal elements of a disposable absorbent article include various types of nonwoven fabrics for the bodyside liner, a thin thermoplastic film for the outer cover and cellulosic fluff for the absorbent batt.

As one type of a disposable absorbent article, diapers presently on the market are flat open-sided garments that are intended to be fitted about an infant while lying down. A diaper is meant for use when the child is young and dependent upon a parent for fitting the diaper on the child.

The popularity of disposable diapers has led us to believe there is a demand for a disposable training pant that can be used when a child grows out of a diaper. Diapers are typically used with infants up to about 15 months old. When a child reaches an age in the range of about 15 to 30 months, a parent generally desires to start toilet training so the child can become independent of the parent. The training pant is intended for use when the child has reached an age at which he or she is ready to graduate to an underpant type of garment as a replacement for disposable diapers previously used. Thus, a suitable training pant must be a garment having closed sides so that a child can raise and lower the garment as necessary without requiring the aid of a parent. At the same time, a training pant must provide features of liquid and solid absorbency and prevent leakage of the waste fluids.

Cloth training pants, although widely used, have disadvantages. Current cloth training pants have very little absorbency and often must be used with exterior rubber or plastic pants. When a child wets a cloth training pant, most often all of the child's clothes must be changed. Further, if a child has a bowel movement, it is difficult to remove a cloth pant without making a mess, and the pant must be soaked and bleached. All of these factors can make the toilet training process frustrating for both child and parent.

Moreover, it is believed that the psychology of the toilet training stage is such that the child should perceive he or she is graduating to a garment that is different than a disposable diaper.

As another type of a disposable absorbent article, some of the currently-used incontinence products for adults and older children have been found unsatisfactory due to their bulkiness and ineffectiveness. Many of these garments are formed by folding flat sheets into a diaper-like structure that is bulky, particularly in the crotch portion. This type of garment further has a tendency to become dislodged during activity. Clearly, for the active person, these diaper-type garments are not desirable since they are bulky and interfere with the movements of the individual and the wearing of ordinary clothes. Furthermore, the large amounts of material utilized requires these adult diaper-type garments to be relatively expensive.

SUMMARY OF THE INVENTION

In one form of the invention, there is provided a disposable pant-like garment for absorbing human discharge comprising an absorbent assembly including a liquid impervious outer cover, a liquid pervious liner, and an absorbent medium therebetween. A pair of stretchable side panels are joined to the absorbent assembly to form a waist opening and a pair of leg openings, and an intermediate portion of each of the stretchable side panels is generally peripherally disposed about a respective one of the leg openings, whereby the side panels provide generally inwardly directed force vectors against a wearer to maintain the garment snugly against the wearer's body and the absorbent assembly snugly in place against the crotch area both before and after a discharge, and the intermediate portions of the stretchable side panels provide elasticity about the leg openings to prevent leakage thereat.

BRIEF DESCRIPTION OF THE DRAWINGS

The above-mentioned one and other features and objects of this invention and the manner of attaining them will become more apparent, and the invention itself will be better understood by reference to the following description of the invention taken in conjunction with the accompanying drawings, wherein:

FIG. 5B;

DETAILED DESCRIPTION

Figure 1:
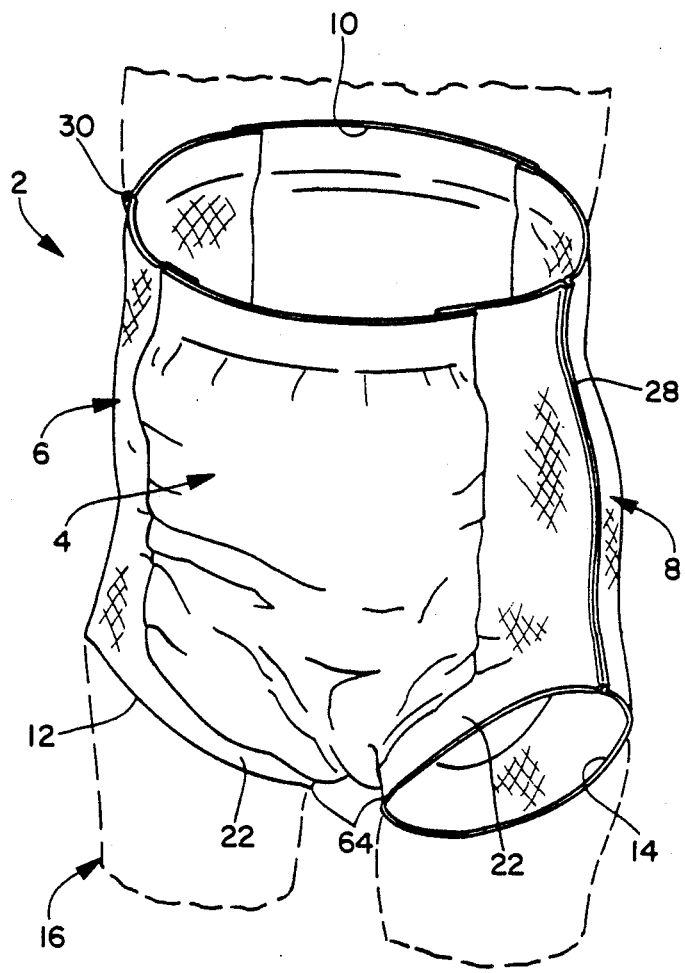
FIG. 1 is a perspective view of a training pant or incontinence garment as it would appear being worn on a wearer indicated in dashed lines.
Figure 2:
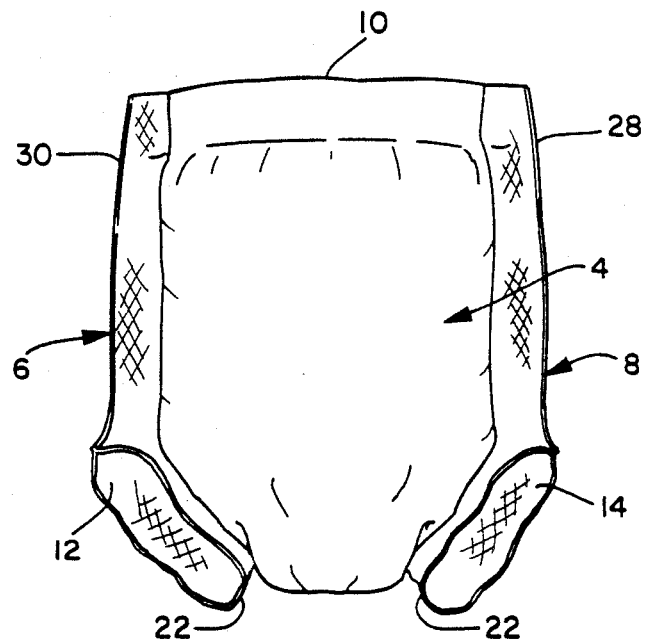
FIG. 2 is a front elevational view of the pant or garment in FIG. 1.
Figure 4:
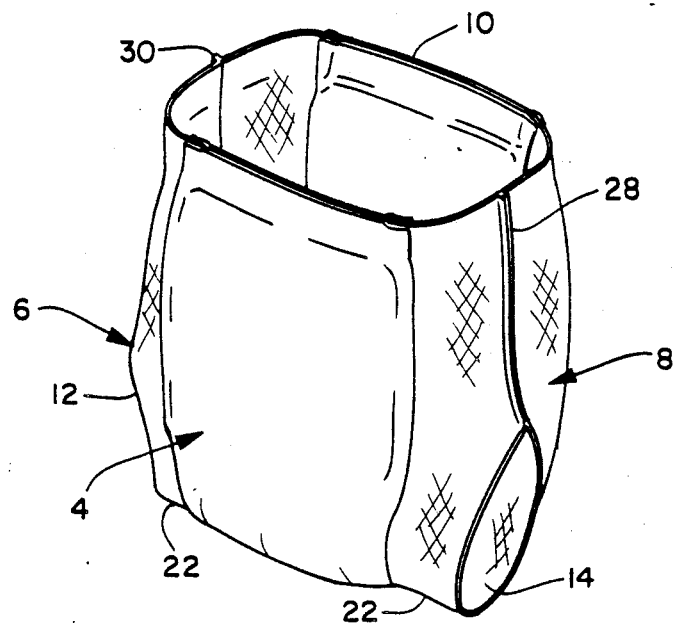
FIG. 4 is a perspective view of the pant or garment of FIG. 1.

Referring to FIGS. 1, 2 and 4, there is illustrated one embodiment of a pant or garment designated absorbent garment 2. Garment 2 generally comprises waste containment section 4 and two elastic or stretchable side panels 6, 8 defining a waist opening 10 and a pair of leg openings 12, 14. The total surface area of both side panels 6, 8 comprise about 20% to about 80% of the total surface area of garment 2, preferably about 25% to about 50%, and more preferably about 35% to about 45%. FIG. 1 illustrates absorbent garment 2 fitted on a wearer's torso portion 16 in dashed lines.

Figure 5:
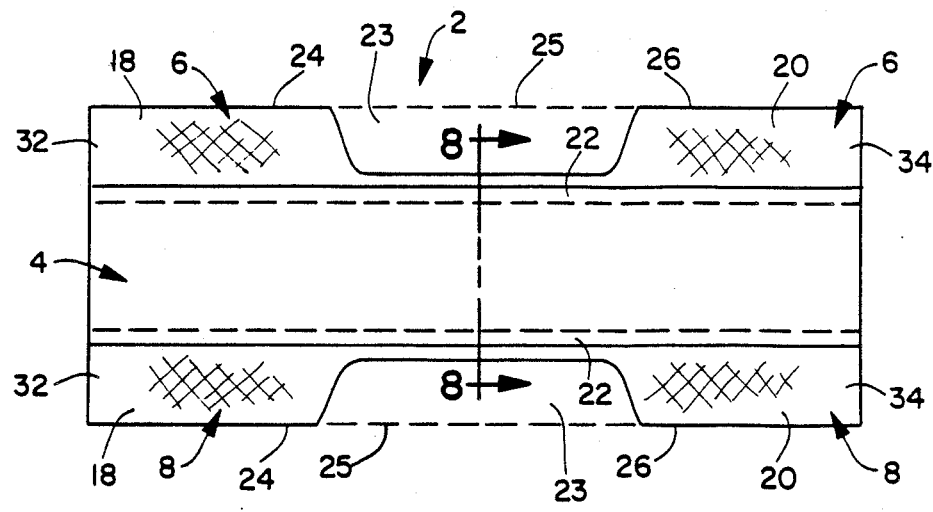
FIG. 5 is a top plan view of the pant or garment of FIG. in a flat condition with leg cut-outs before the seams are joined.

Referring now to FIG. 5, absorbent garment 2 is illustrated in a two-dimensional or planar configuration it assumes during the manufacturing process. Elastic side panels 6, 8 are joined to waste containment section 4, and each side panel 6, 8 includes relatively wide end portions 18, 20 being joined by relatively narrow intermediate portions 22, thereby forming leg cut-outs 23. When the remote edges 24 of respective end portions 18 are joined to remote edges 26 of respective end portions 20 to form seams 28, 30 (FIG. 1), stretchable intermediate portions 22 provide elasticity for leg openings 12, 14. Similarly, when end portions 18 are joined to end portions 20, remote end segments 32 of end portions 18 and remote end segments 34 of end portions 20 provide elasticity to waist opening 10. Generally, each side panel will have a length of about 12 inches to about 30 inches, and a width from about ½ inch to about 6 inches. The total garment length is generally the same as the total length of a side panel.

Hereafter, the terms "elasticity," "stretchability," and "elongation" will be interchangeably used to describe the properties of various materials. The meaning of these three words is intended to be the same, and that is that the material can be stretched and, upon relaxing, will tend to resume its original shape.

If desired, narrow intermediate portions 22 can be eliminated, i.e., not manufactured into garment 2, so that end portions 18, 20 extend as one integral portion along dashed lines 25. Portions 18, 20 would still be joined as described above to form leg openings 12, 14. That is, the intermediate portions of portions 18, 20 indicated by dashed lines 25 would not be bonded.

As mentioned earlier, side panels 6, 8, which include end portions 18, 20 and intermediate portion 22, have elastic or stretchable properties. Side panels 6, 8 can be made of a single layer of woven or nonwoven elastic or stretchable material, such as block copolymers of polystyrene, polyisoprene or polybutadiene copolymers of ethylene, natural rubbers, urethanes, Kratons and coextrusions/blends of the aforementioned. Other examples of suitable elastomeric materials include copolymers of ethylene, EVA (ethylene-vinyl acetate), EEA (ethylene-ethyl acetate), EAA (ethylene-acrylic acid) and EMA (ethylene-methyl acrylate) and various percent blends of the copolymers of ethylene with polypropylene. Co-extruded composites of EVA (ethylene-vinyl acetate), EEA (ethylene-ethyl acetate), EAA (ethylene-acrylic acid) and EMA (ethylene-methyl acrylate) and polypropylene at various percents or mil thicknesses could also be used as the elastic material. Also, elastomeric staple integrated composites where staple fibers such as polypropylene, polyester, cotton or any other suitable staple fiber are integrated into an elastomeric meltblown web. Stretchable side panels 6, 8 can also be a film of elastomeric material.

The above elastomeric materials may be formed by any suitable processes, such as film extrusion, spunbond process, meltblown process and the like.

Figure 6:
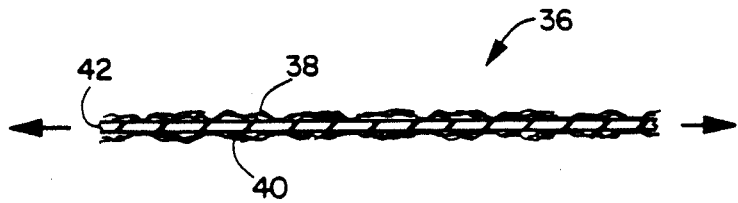
FIG. 6 is a fragmentary, side cross-sectional view of a stretch-bonded laminate in the stretched condition.
Figure 7:
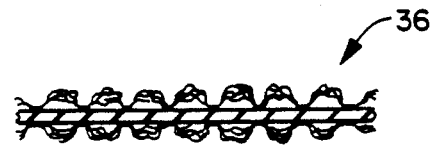
FIG. 7 is a fragmentary, side cross-sectional view of the stretch-bonded laminate of FIG. 6 in a relaxed condition.

Side panels 6, 8 can also be a stretch-bonded laminate that may have elasticity in all directions, and may be breathable, i.e., is pervious to vapors, but impervious to liquids. FIGS. 6 and 7 illustrate a stretch-bonded laminate 36 in the stretched and relaxed conditions, respectively. Stretch-bonded laminate 36 generally comprises an outer layer 38, an inner bodyside layer 40 and an elastic or stretchable layer 42 disposed between layers 38, 40. Although 38, 40 are described as outer and inner, respectively, they can be made of the same materials, and thus be interchangeable.

Layers 38, 40 can be made of any woven or nonwoven material, and are preferably made of a nonwoven fibrous material. Examples of nonwoven fibrous material include variously bonded polyolefin fibers such as thermally-bonded polypropylene, polyethylene, polyester; spunbonded polypropylene, spunbonded polyethylene or blends thereof; meltblown polypropylene, meltblown polyethylene or blends thereof; bonded carded webs of synthetic or natural fibers or blends thereof; extruded films of thermoplastic materials; and the like. Naturally, copolymers of polyolefin or other material fibers may also be utilized.

Elastic or stretchable layer 42 can be a meltblown or film of block or graft copolymers such as butadiene, isoprene, styrene, ethylene-methyl acrylate, ethylene-vinyl acetate, ethylene-ethyl acrylite or blends thereof. One preferred elastomeric is a block copolymer of styrene-ethylbutadiene-styrene. Other types of materials of which elastic layer 42 can be made are the Kraton G series from The Shell Chemical Company such as Kraton G-1650, Kraton G-1652, Kraton GX-1657 and preferably Kraton G-2740X Also, the Kraton D series can be used, as well as polyester elastomeric materials, polyurethane elastomeric materials and polyamide elastomeric materials.

It should be pointed out at this point that the stretchable or elastomeric materials of which side panels 6, 8 are made can also be used for layer 42, and the just-described stretchable or elastomeric materials of which layer 42 can be made may also be used to make side panels 6, 8.

Typically, a stretch-bonded laminate is made by stretching the elastic or stretchable layer 42 to a selected elongation; placing a nonstretched layer, such as layer 38 or 40 or both, on the stretched layer 42; bonding the layers together and allowing the layers to relax so that layer 42 gathers the other layers.

Figure 8:
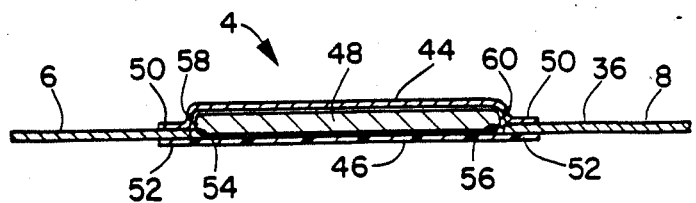
FIG. 8 is a sectional view of FIG. 5 taken along line 8—8 and viewed in the direction of the arrows.

Referring now to FIG. 8, which is a cross-section through FIG. 5, the attachment of waste containment section 4 with side panels 6, 8 is illustrated. Waste containment section 4 generally comprises a fluid-pervious bodyside liner 44, a liquid-impervious outer cover 46 and an absorbent medium 48 between liner 44 and cover 46. Outer cover 46 can be a woven or nonwoven material-film, or a film-coated nonwoven material comprising cast or blown films of polyethylene, polypropylene, polyester or blends thereof. Outer cover 46 may also be a composite of a bonded carded or spunbonded or meltblown material, for example, a bonded carded-film composite, or a spunbonded-meltblown composite of thermoplastic material, or a spunbonded-meltblown-spunbonded thermoplastic material, wherein the spunbonded layer can provide a cloth-like texture and the meltblown layer can provide liquid impermeability. Materials of which outer cover 46 can be made include nonwovens having a high basis weight, such as about 0.4 ounces per square yard, about 10 grams per square meter or basis weights greater than the aforementioned. Outer cover 46 can also be extruded films of polyolefin polymers or copolymers or other thermoplastic materials. Generally outer cover 46 will have a length from about 12 inches to about 30 inches, and a width from about 3 inches to about 20 inches.

Bodyside liner 44 can be a woven material, or a nonwoven material such as any flexible porous sheet of polyolefin fibers, such as polypropylene or polyethylene or polyester fibers; a web of spunbonded polypropylene or polyethylene or polyester fibers; a web of rayon fibers; a bonded carded web of synthetic or natural fibers or blends thereof. Liner 44 can also be an apertured plastic film. Liner 44 generally will have a length from about 12 inches to about 30 inches, and a width from about 3 inches to about 20 inches.

Absorbent medium 48 can be made of wood pulp fluff or a mixture of wood pulp fluff and a superabsorbent material, or a wood pulp fluff integrated with a thermoplastic absorbent material treated with a surfactant. Thermal binders, such as Pulpex ® can be used in blends or layering with the fluff and superabsorbent. Medium 48 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins. Medium 48 generally will have a length from about 12 inches to about 30 inches, and a width from about 3 inches to about 20 inches.

As illustrated in FIG. 8, outer cover 46 and bodyside liner 44 sandwich absorbent medium 48, which is preferably adhered only to outer cover 46 by any suitable adhesive or other means. Alternatively, absorbent medium 48 could be joined to bodyside liner 44 or both bodyside liner 44 and outer cover 46. The longitudinal edge portions 50 of bodyside liner 44 and the longitudinal edge portions 52 of outer cover 46 also sandwich respective edge portions of side panels 6, 8 to join them to waste containment section 4. Side panels 6, 8 can be joined or adhered between respective edge portions 50, 52 by heat sealing, ultrasonic sealing, adhesive sealing or by other conventional means, such as stitching and the like.

As illustrated in FIG. 8, side panels 6, 8 have respective panel inner sides 54, 56 that are illustrated as being just slightly spaced apart from respective absorbent sides 58, 60. One of the unique features of the present invention is the positional relationship between the panel inner sides 54, 56 and absorbent sides 58, 60. Depending on the degree of elasticity and the amount of gathering desired, the panel inner sides 54, 56 can be positioned at different distances from respective absorbent sides 58, 60. For example, panel inner sides 54, 56 can be in direct abutment against absorbent sides 58, 60 to provide maximum gathering, or panel inner sides 54, 56 can be spaced apart from respective absorbent sides 58, 60 as desired. A desired range of distances between panel inner sides 54, 56 and respective absorbent sides 58, 60 is 0 to about 2 inches. A preferred range is from 0 to about 1 inch, and a more preferred range is from 0 to about ½ inch. Alternatively, panel inner sides 54, 56 could overlap or extend over or under absorbent sides 58, 60.

When panel inner sides 54, 56 are in abutment against absorbent sides 58, 60, the effect is to provide additional seal against leakage, and allow for a more uniform transition from side panel to absorbent.

Figure 9:
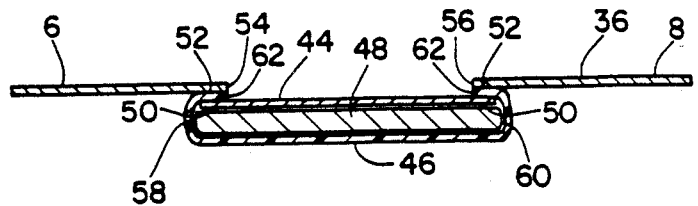
FIG. 9 illustrates a modification of the view of FIG. 8.

As the panel inner sides 54, 56 are spaced an increasing distance from absorbent sides 58, 60, the resulting effect is to allow additional flexibility to the leg gasketing at each leg opening Referring to FIG. 9, there is illustrated a modification to the structure of FIG. 8. The longitudinal edge portions 50 of bodyside liner 44 terminate substantially at absorbent sides 58, 60. Longitudinal edge portions 52 of outer cover 46 overlap absorbent sides 58, 60 and edge portions 50 to form liquid-impervious baffles 62. Side panels 6, 8 are then joined on top of edge portions 52, which form baffles 62, such that edge portions 52 of outer cover 46 are joined between respective side panels 6, 8 and bodyside liner 44. As illustrated in FIG. 9, panel inner sides 54, 56 of side panels 6, 8 are substantially coincident with the remote ends of edge portions 52. If desired for better fluid control, baffles 62, which again are the overlapping edge portions 52 of outer cover 46, can extend further inwardly over bodyside liner 44 and beyond panel inner sides 54, 56, thereby creating larger baffles 62. By so extending baffles 62 toward the central portion of absorbent medium 48, there is a reduction in the amount of fluid flowback that may occur in both the longitudinal and transverse directions, thereby further reducing the chance of any fluid leakage about the leg openings 12, 14.

Figure 10:
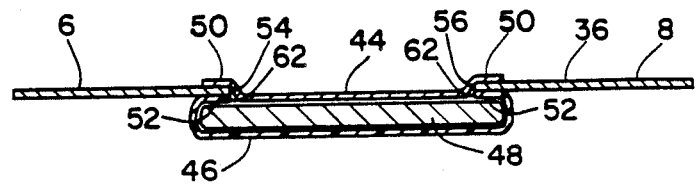
FIG. 10 illustrates a modification of the view of FIG. 8.

Referring to FIG. 10, another modification of FIG. 8 is illustrated. In this particular modification, edge portions 52 of outer cover 46 overlap only absorbent medium 48. Side panels 6, 8 are then attached to the top of edge portions 52, again which form baffles 62, and bodyside liner 44 is then attached to side panels 6, 8. As illustrated in FIG. 10, panel inner sides 54, 56 are substantially coincident with the ends of edge portions 52. However, edge portions 52, forming baffles 62, can extend further inwardly toward the center of absorbent medium 48, thereby providing greater protection against fluid flowback in both the longitudinal and transverse directions.

The percentage of overlap or coverage of absorbent medium 48 by baffles 62 can be 0 to about 99%, preferably about 10% to about 50%, and more preferably about 10% to about 20%.

As baffles 62 are disposed further inwardly toward the center of absorbent medium 48, panel inner sides 54, 56 of side panels 6, 8 can likewise be extended further inwardly before being joined to edge portions 52. The percent overlap or coverage of panel inner sides 54, 56 over absorbent medium 48 can be 0 to about 50%, preferably about 3% to about 20%, and more preferably about 6% to about 12%.

With reference to FIGS. 9 and 10, side panels 6, 8 alternatively can be attached to the bottom surface of outer cover 46.

As described above, waste containment section 4 of absorbent garment 2 is maintained in a snug-fitting, comfortable fashion against the wearer by elastic or stretchable side panels 6, 8. The effect of elastic or stretchable side panels 6, 8, which may also include the intermediate portion 22 extending about the inner portion of the wearer's legs, is to provide not only vertical forces that maintain the waste containment section 4 against the wearer's crotch area, but also inwardly directed horizontal force vectors against the hips and mid-section that hold or hug waste containment section 4 against the sides of the wearer, both before and after a void.

Figure 1A:
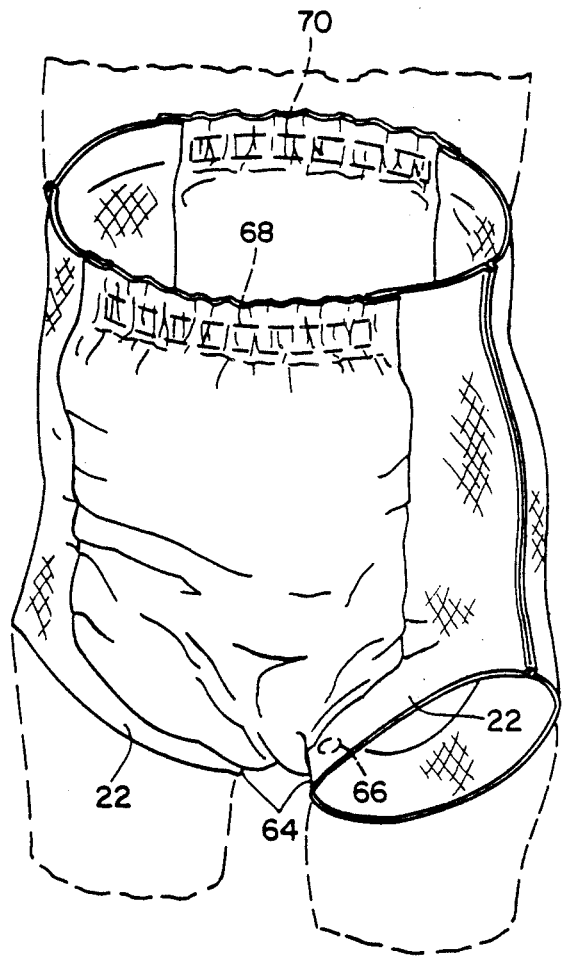
FIG. 1A is a perspective view of another pant or garment on a wearer indicated in dashed lines.
Figure 4A:
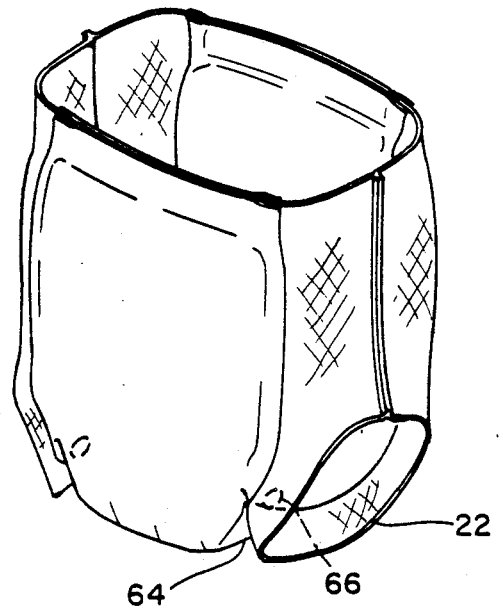
FIG. 4A is a perspective view similar to FIG. 4 illustrating a modification thereto.

Another unique feature of the present invention is illustrated in FIGS. 1, 1A and 4A wherein intermediate portions 22 of elastic side panels 6, 8 form a pair of gussets 64. As illustrated in FIG. 1A, and in a more exaggerated manner in FIG. 4A, intermediate portions 22 are generally flat or planar in the transverse dimension, and curvilinear in the longitudinal dimension so as to conform to the wearer's leg. When absorbent garment 2 is properly fitted on the wearer, as illustrated in FIG. 1, each intermediate portion 22 tends to fold or tuck on itself to form a respective gusset 64 at the wearer's crotch area. This double tuck or gusset 64 provides additional gasketing about leg openings 12, 14, thereby further reducing the potential of fluid leakage, particularly during movement of the wearer.

The width or transverse dimension of each intermediate portion 22 is generally a function of the maximum width of its respective side panels 6, 8. The width of intermediate portion 22 can be about 5% to about 100% the maximum width of its side panel, preferably about 20% to about 80%, and more preferably about 30% to about 50%.

Gussets 64 can be preformed during the manufacturing of absorbent garment 2 by means of dots 66 of adhesive (FIGS. 1A and 4A). Dots 66 can also be formed by heat sealing, ultrasonic sealing or any other conventional means of attachment. The formation of gussets 64 with dots 66 can be made between the inner edge of portion 22 and the outer edge of portion 22, or between a transversely intermediate portion of portion 22 and an edge portion of waste containment section 4.

Figure 3:
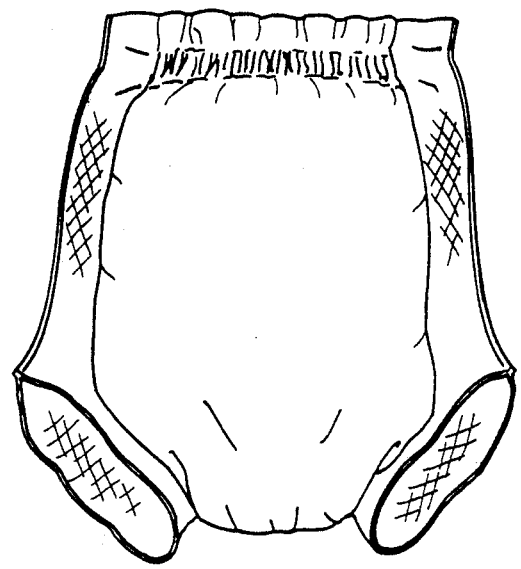
FIG. 3 is a front elevational view of the pant or garment in FIG. 1A.
Figure 5A:
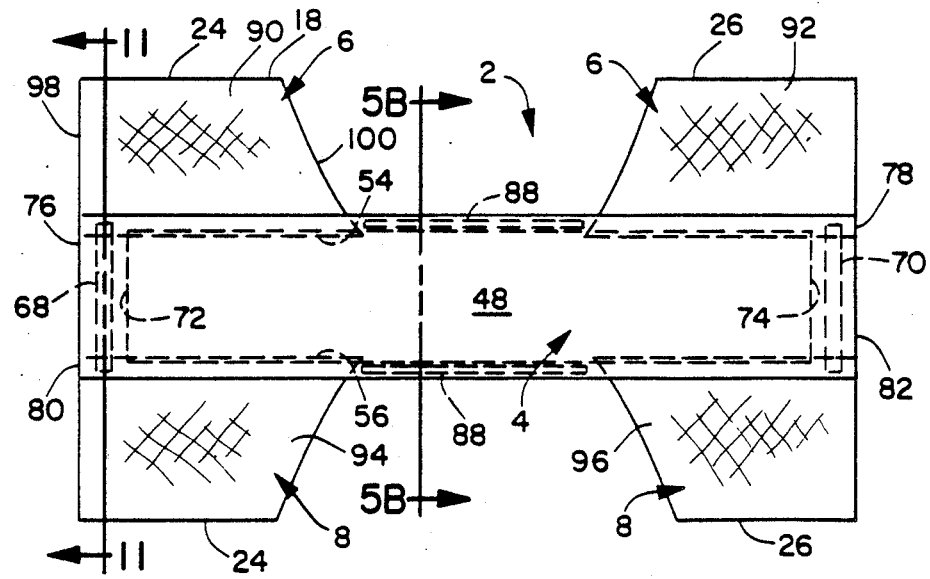
FIG. 5A illustrates a modification to the pant or garment in FIG. 5.

Referring now to FIGS. 1A, 3, and 5A, there is illustrated a modification of absorbent garment 2 in FIG. 1 by the addition of waist elastic 68 at the front of garment 2 and waist elastic 70 at the back of garment 2. Waist elastics 68, 70 can provide additional elastic stretch in the waist for better fit and additional leakage control Referring to FIG. 5A, waist elastics 68, 70 are illustrated with absorbent garment 2 in a two-dimensional or planar form before the construction of seams 28, 30. Ends 72, 74 of absorbent medium 48 terminate short of outer cover ends 76, 78 and bodyside liner ends 80, 82. Absorbent ends 72, 74 are spaced a distance from outer cover ends 76, 78 in the range of about ⅛ inch to about 2 inches. Generally, bodyside liner ends 80, 82 are substantially coincident with outer cover ends 76, 78, and the total length of the garment is measured between these ends. It may be that bodyside liner ends 80, 82 extend beyond outer cover ends 76, 78 and are folded over ends 76, 78 to form a skirt or fringe about waist opening 10. In this case, the total garment length is measured between ends 76, 78. Similarly, outer cover ends 76, 78 could extend beyond bodyside liner ends 80, 82 and be folded thereover, and the total garment length is measured between ends 80, 82.

Preferably, waist elastics 68, 70 are made of an activatable elastic material applied in an unstretched condition. Thereafter, waist elastics 68, 70 are activated, such as by heat, light, moisture
or the like, so as to retract and become elastic. Types of these activatable elastic materials can be purchased from the Minnesota Mining and Manufacturing Company.

Each waist elastic 68, 70 can be a single ribbon of elastic material that is suitably adhered solely to bodyside liner 44, or to outer cover 46, or to both liner 44 and cover 46. A single ribbon of waist elastic 68 or 70 in the relaxed, attached condition has a length of about 2 inches to about 12 inches and a relaxed, attached width of about ¼ inch to about 2 inches. Generally, waist elastics 68, 70 will be adhered in a stretched condition, and in the stretched condition, each waist elastic 68, 70 will have a stretched length of about 2¼ inches to about 15 inches and a stretched width of about ⅛ inch to about 1⅛ inches. These parameters should provide a relaxed, attached length of about 50% to about 100% of the width of waste containment section 4.

Instead of each waist elastic 68, 70 being a single ribbon of elastic material, each may be comprised of a multiple strand of ribbons having a generally rectangular cross-section or ropes having a generally circular or arcuate cross-section. For example, if each waist elastic 68, 70 comprises multiple strands of ribbons, each of the ribbons in the strand will have a length similar to those for a single ribbon and a width from about ⅛ inch to about ¾ inch. If each waist elastic 68, 70 comprises multiple strands of rope elastics, each rope preferably will have a length similar as above and a width or diameter from about 0.04 inches to about 0.25 inches.

Waist elastics 68, 70 may be made of any suitable elastic material, such as those of which side panels 6, 8 or stretchable layer 42 can be made. Suitable adhesives for adhering waist elastics 68, 70 to absorbent garment 2 include hot melt adhesives, spray adhesives, self-adhering elastomeric materials and the like.

Figure 11:
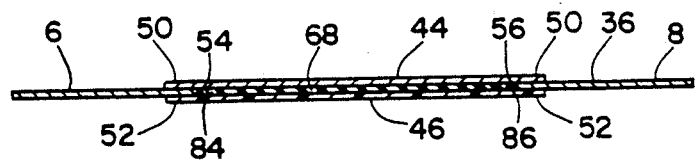
FIG. 11 is a sectional view of FIG. 5A taken along line 11—11 and viewed in the direction of the arrows.
Figure 12:
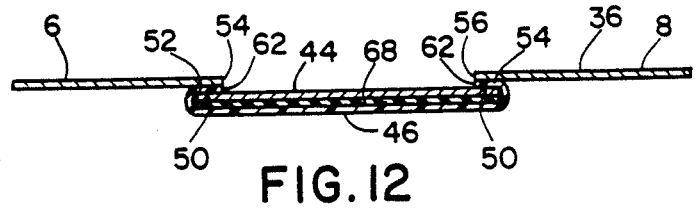
FIG. 12 illustrates a modification of the view of FIG. 11.
Figure 13:
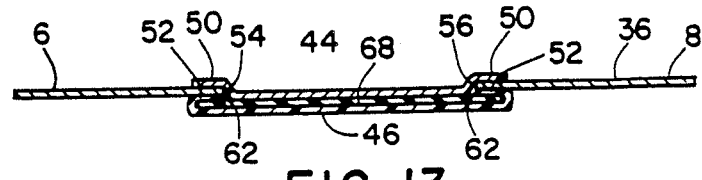
FIG. 13 illustrates a modification of the view of FIG. 11.

Referring now to FIGS. 11–13, the various seam configurations for waist elastics 68, 70 will be described. Since both waist elastics 68, 70 can be attached in a similar manner, only a description of waist elastic 68 will be made with the understanding that it also applies to waist elastic 70. In FIG. 11, waist elastic 68 is sandwiched between bodyside liner 44 and outer cover 46. Similarly, side panels 6, 8 are sandwiched between bodyside liner 44 and outer cover 46, with panel inner sides 54, 56 abutting against respective waist elastic sides 84, 86. The attachment of waist elastic 68 and panels 6, 8 to bodyside liner 44 and outer cover 46 can be made by heat sealing, ultrasonic sealing, adhesive sealing or any other suitable means. In FIG. 11, panel inner sides 54, 56 abut against respective waist elastic sides 84, 86 in order to provide a continuous stretchable or elastic effect about the periphery of waist opening 10. However, panel inner sides 54, 56 can be spaced from respective waist elastic sides 84, 86 in the range of 0 inches to about 2 inches. A preferred range is from 0 to about 1 inch, and a more preferred range is from 0 to about ½ inch. Also, side panel inner sides 54, 56 could overlap partially or completely waist elastics 68, 70 in that area between outer ends 76, 78 and absorbent ends 72, 74 (FIG. 5A).

Referring now to FIG. 12, the sides of waist elastic 68 and bodyside liner 44 are substantially coincident, and longitudinal edge portions 52 of outer 46 are folded to overlap longitudinal edge portions 50 of bodyside liner 44, thereby forming baffles 62. Side panels 6, 8 are then adhered to the exposed tops of baffles 62, such that panel inner sides 54, 56 are substantially coincident with the ends of baffles 62. Baffles 62 can be extended further inwardly toward the center portion of bodyside liner 44 to accommodate the modification described with reference to FIG. 9, wherein baffles 62 extend further inwardly of absorbent medium 48. The percentage of coverage or overlap of baffles 62 over waist elastics 68, 70 and bodyside liner 44 can be 0 to about 100%. Preferably, the coverage or overlap is about 5% to about 50%, and more preferably about 8% to about 13%.

Referring now to FIG. 13, longitudinal edge portions 52 of outer cover 46 overlap waist elastic 68 to form baffles 62, and side panels 6, 8 are then adhered to baffles 62. Bodyside liner 44 is disposed over waist elastic 68 and side panel inner sides 54, 56. Baffles 62 can extend over elastic 68 as described above with reference to FIG. 12.

Referring now to FIG. 5A, there is illustrated another modification of absorbent garment 2 wherein elastic intermediate portions 22 have been eliminated and leg elastics 88 substituted therefor. Leg elastics 88 may be made of the same or other described materials of which waist elastics 68, 70 can be made. Leg elastics 88 may be similarly adhered by one of those methods described for adhering waist elastics 68, 70. Each leg elastic 88 is preferably a single ribbon of elastic material having a relaxed, attached length of about 1 inch to about 18 inches, and a relaxed width of about ⅛ inch to about 3 inches, and an elongation of about 25% to about 350%. A preferred length is about 2 inches to about 9 inches and an elongation of about 30% to about 260%. A more preferred length is about 3 inches to about 4 inches and an elongation of about 125% to about 200%. A preferred relaxed width is about ¼ inch to about 1½ inches, and a more preferred width is about ½ inch to about 1 inch.

As a percentage of total garment length, the relaxed, attached elastic 88 has a length of about 10% to 100% of total garment length. A preferred length is about 10% to about 50%, and a more preferred length is about 15% to about 25%.

As with waist elastics 68, 70, leg elastics 88 do not necessarily need to be a single ribbon of elastic material, but can be multiple strands of ropes or ribbons of elastic material. If elastics 88 are rope-like, preferred diameters are between about 0.04 inches to about 0.25 inches.

Figure 5B:
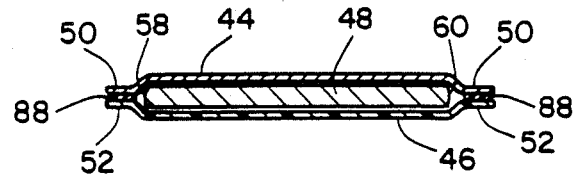
FIG. 5B is a sectional view of FIG. 5A taken along line 5B—5B.

Referring to FIG. 5B, leg elastics 88 are positioned between longitudinal edge portions 50 of bodyside liner 44 and longitudinal edge portions 52 of outer cover 46. Leg elastics 88 can abut against or be spaced apart from respective absorbent sides 58, 60.

Figure 5C:
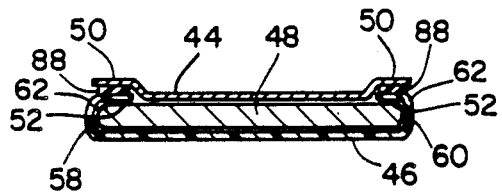
FIG. 5C illustrates a modification of the view in FIG.

FIG. 5C illustrates a modification of the placement of leg elastics 88. In this modification, outer cover 46 is wrapped around absorbent edges 58, 60 so as to overlap and form baffles 62. Leg elastics 88 are then positioned on top of baffles 62, which are also longitudinal edge portions 52, and bodyside liner 44 is then disposed over leg elastics 88.

Figure 5D:
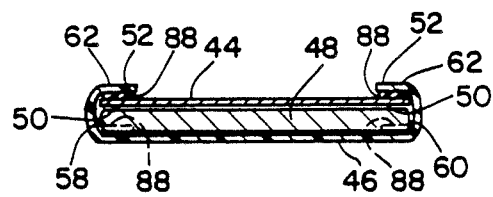
FIG. 5D illustrates another modification of the view of FIG. 5B.

Similarly, FIG. 5D illustrates leg elastics being positioned on top of longitudinal edge portions 50 of bodyside liner 44, and with outer cover 46 then overlapping leg elastics 88 to form baffles 62.

Also, in both the modifications illustrated in FIGS. 5C and 5D, leg elastics 88 may be positioned below absorbent medium 48, as illustrated in dashed lines in FIG. 5D. In this case, leg elastics 88 would be positioned between outer cover 46 and absorbent medium 48. In FIG. 5B, leg elastics 88 can also be positioned either above or below absorbent medium 48.

When leg elastics 88 are used with garment 2, elastic side panel 6 will comprise two elastic side sections 90, 92 (FIG. 5A) and elastic side panel 8 will comprise elastic side sections 94, 96. With the modification of absorbent garment 2 illustrated in FIG. 5A being symmetric about both its longitudinal and transverse axes, each elastic side section 90, 92, 94, 96 will be identical in dimensions. In this particular case where absorbent garment 2 is symmetrical about its axes, a description of only elastic side section 90 will be made since the other side sections 92, 94, 96 are identical. Elastic side section 90 includes a remote edge 24, panel inner side 54, waist end 98 and arcuate side 100. Generally, the length of remote edge 24 is a function of the total garment length. For example, a desired length of remote edge 24 is about 5% to about 50% of the total garment length, a preferred length is about 15% to about 40% of the total garment length, and a more preferred length is about 30% to about 40% of the total garment length.

In the previous paragraph, the modification to absorbent garment 2 of FIG. 5A was described as being symmetric about its longitudinal and transverse axes. However, the present invention contemplates that the construction of the front portion of absorbent garment 2 may differ from the construction of its back portion. Accordingly, for purposes of explanation, it will be assumed that the left portion of absorbent garment 2 illustrated in FIG. 5A is the front portion, and the right portion of FIG. 5A is the back portion. In this particular case, elastic side sections 90, 94 will be identical to each other, but different from elastic side sections 92, 96, which in turn will be identical to each other. In this modification of garment 2 in FIG. 5A, sections 90, 94 and sections 92, 96 can take any size or configuration as necessary or desired within the above parameters. Generally speaking, the back portion, i.e., sections 92, 96, will be of greater surface area than sections 90, 94.

The present invention also contemplates the use of both intermediate portions 22 with leg elastics 88 in a suitable positional relationship. For example, intermediate portions 22 and leg elastics 88 can overlap, abut at their edges, or be spaced apart.

As explained above, absorbent garment 2 is designed to fit a large range of sizes merely by changing the dimensions of elastic side panels 6, 8, or by changing the type of elastic material of which side panels 6, 8 are made. Generally, the range of sizes can be varied by (1) selecting a material having a desired modulus of elasticity, and/or (2) increasing the length and width dimensions of a given elastic material of which side panels 6, 8 are made. Side panels 6, 8 will generally have a width of about ½ inch to 6 inches, and will be made of a material having an elongation or elasticity from about 10% to about 500%. Preferably, side panels 6, 8 will have a width from about 2 inches to about 3½ inches, and the material of which they are made will have an elasticity between about 50% to about 300% In a more preferred embodiment, side panels 6, 8 will have a width of about 1¼inches to about 2 inches, and an elasticity from about 75% to about 200%.

Figure 15:
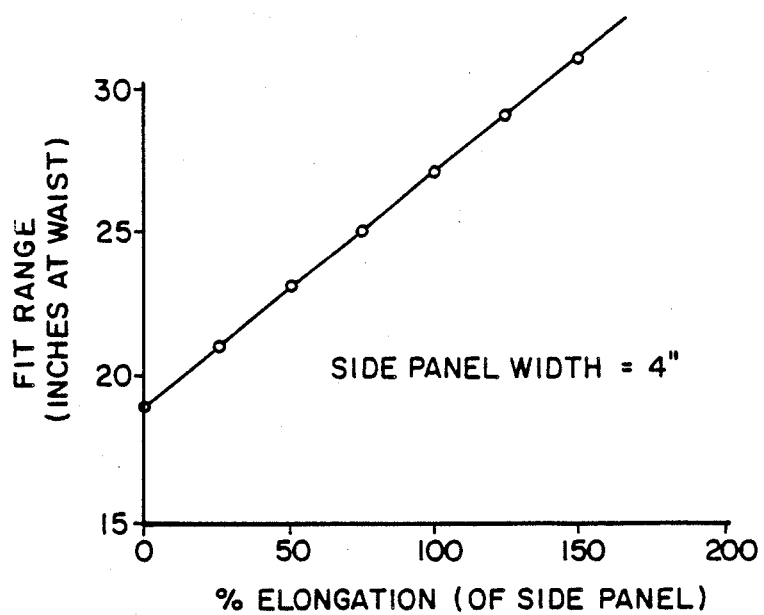
FIG. 15 is a graph of percent elongation of a side panel versus fit range of the waist in inches.
Figure 16:
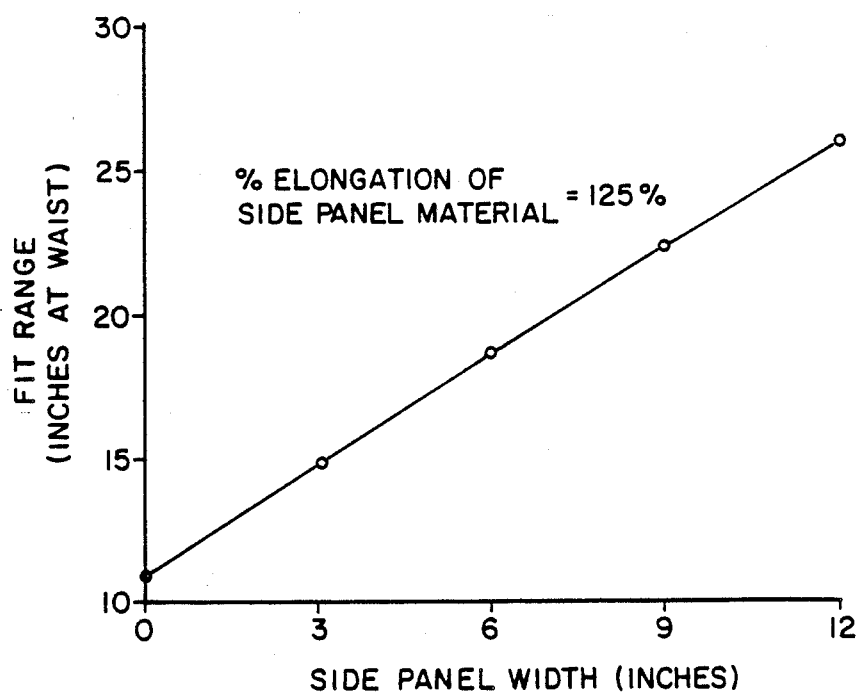
FIG. 16 is a graph of the side panel width in inches versus the fit range at the waist in inches.
Figure 17:
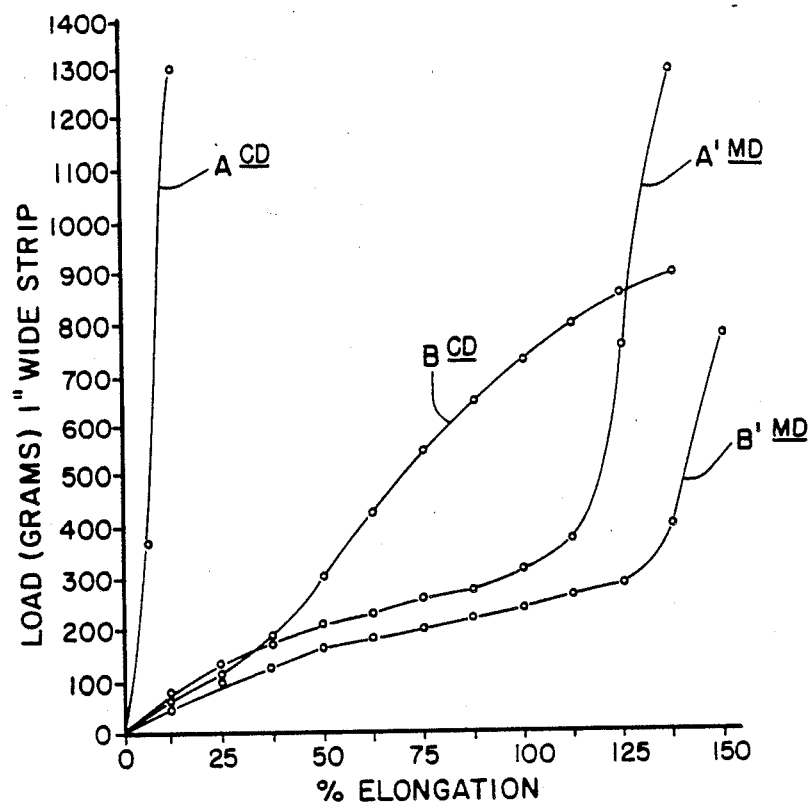
FIG. 17 is a graph of percent elongation versus the load in grams for a one inch wide strip of side elastic.

Referring to FIGS. 15-17, the relationships between side panels 6, 8 and the range of fit sizes of absorbent garment 2 are graphically illustrated. In FIG. 15, each side panel 6, 8 has a width of about 4 inches, and the percent elongation of the side panels is plotted against the fit range in inches at the waist. As illustrated, there is a general linear relationship between the percent elongation of the elastic material of which side panels 6, 8 are made and the size range of the waist measured in inches FIG. 16 illustrates the relationship between side panel width and the fit range in inches at the waist for an elastic material having a percent elongation of 125%. As illustrated, there is a general linear relationship between an increase in the side panel width in inches versus the fit range in inches at the waist.

FIG. 17 is a graph plotting percent elongation versus the load in grams on a 1 inch wide strip of elastic material. The load in grams measures the tension at elongation of the particular material, and this feature is maximized by theoretically having a slope of zero for each plot. In FIG. 17, the plotted curves represent 2 elastic materials, wherein curve A represents the cross-direction stretch and curve A′ represents the machine-direction stretch of one material; and curve B represents the cross-direction stretch and curve B′ represents the machine-direction stretch of the other material. The machine direction stretch, preferably in the stretch-bonded laminate embodiment, is the force vector applied horizontally inwardly toward the hips and mid-section of the garment when worn. This stretch-strain relationship is important to the use and performance of the garment. The side panel material must stretch to adjust to various sizes. The tension cannot be so high that the garment is difficult to use or be too tight during use. Nor, can it be so low in tension as not to maintain the product in position during use. Preferably, the materials of which side panels 6, 8 are made will have a tension range, load (grams) per 1-inch wide strips, from 50 grams to 1,000 grams. In a more preferred embodiment, the side panel materials would have a tension range of about 200 to about 500 grams per 1-inch wide strip. Secondly, curves A′ and B′ both illustrate relatively very gradual slopes between 0 and about 125% elongation. The slope is important to maintain a constant fit tension at the various sizes. With a theoretical slope of 0, the tension of the product would be the same at the relaxed size as it would be at the fully-stretched size.

Figure 18:
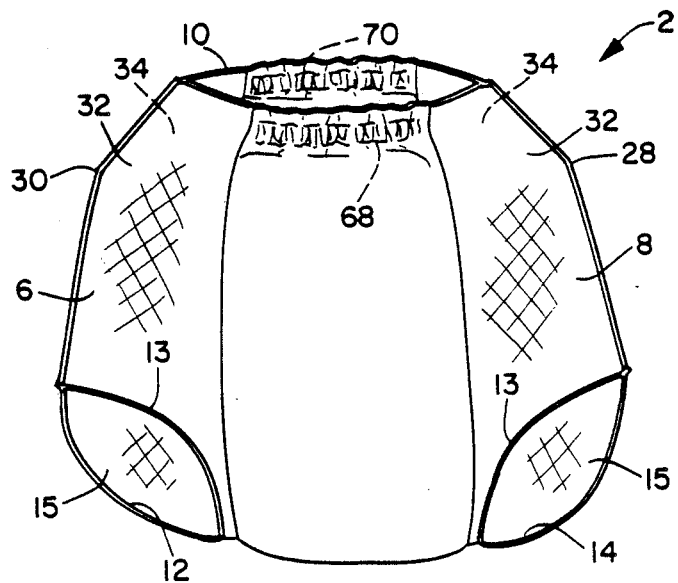
FIG. 18 illustrates yet another pant or garment.

Referring now to FIG. 18, there is yet another modification of absorbent garment 2 that includes waist elastics 68, 70. A unique feature of this modification of absorbent garment 2 is the geometry of elastic side panels 6, 8. Specifically, it can be seen that the front portions 13 of leg openings 12, 14 are cut higher than the back portions 15 of leg openings 12, 14. The purpose for this particular geometry of leg openings 12, 14 is to improve further the fit of the garment. The added material in the back provides coverage of the buttocks, while in the front the cut is higher in following the curvature of the leg, thereby permitting freer leg movement.

The upper portions of elastic side panels 6, 8 are identified as remote end segments 32, 34, and they are cut so that they slope inwardly and upwardly from the intermediate portions of side panels 6, 8 toward waist opening 10. The purpose for this is to improve further the fit of the garment, especially when the user is disproportionate at the hips and waist. The design or configuration also assists in pulling the garment up in place. The length of each sloping end segment 32, 34 is from about 3% to about 40% of the total garment length, preferably about 5% to about 25% of total garment length, and more preferably about 10% to about 15% of total garment length.

The angular slope, as measured with the vertical in FIG. 18, of end segments 32, 34 is from about 5° to about 55°, preferably from about 10° to about 40°, and more preferably from about 15° to about 30°.

Figure 14:
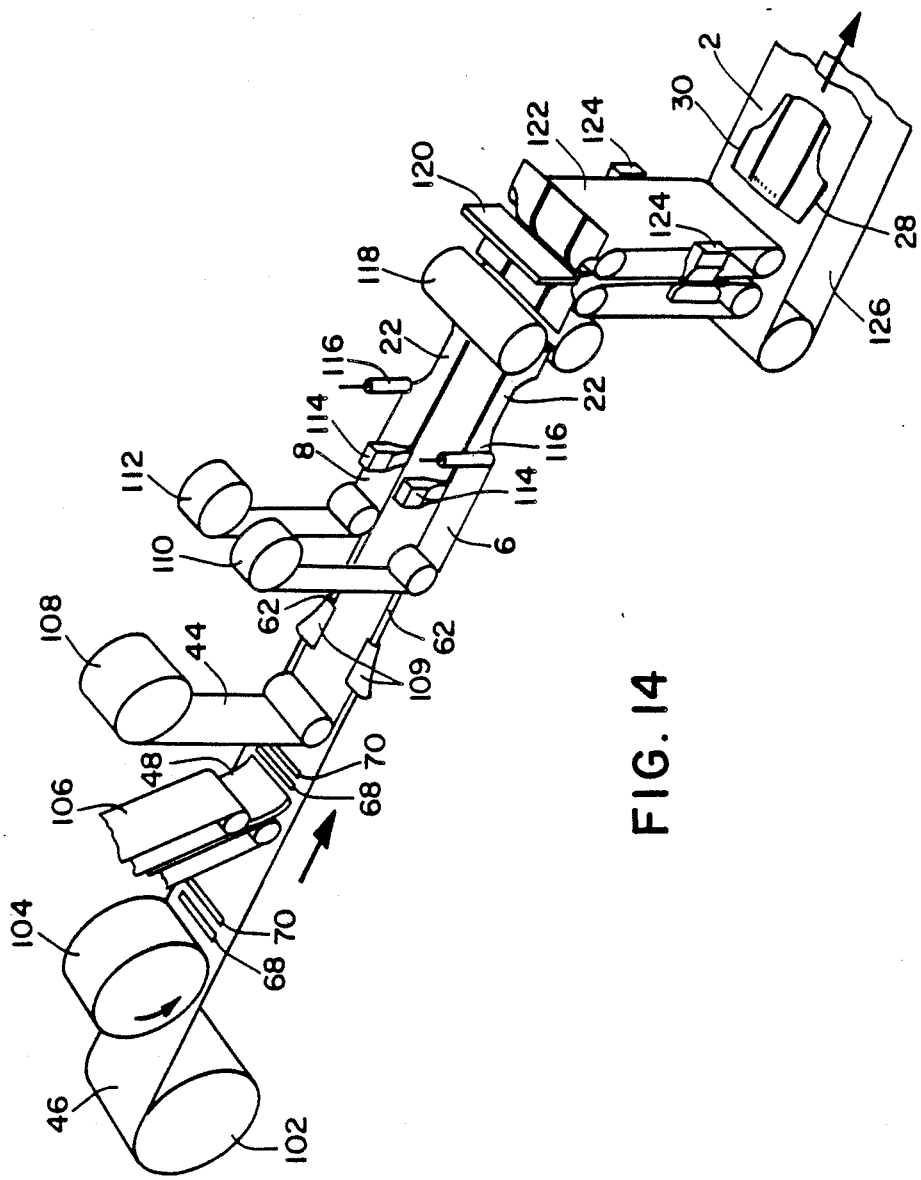
FIG. 14 is a schematic of one apparatus for producing one embodiment of a pant or garment.

Referring now to FIG. 14, a description will be made of one process for making one embodiment of a pant or garment. Supply roll 102 provides a continuous supply of outer cover 46 to supply drum 104, which attaches, if desired, waist elastics 68, 70 thereon. After application of waist elastics 68, 70, outer cover 46 continues to conveyor assembly 106 which positions absorbent medium 48 between waist elastics 68,70. Thereafter, supply roll 108 delivers a continuous supply of bodyside liner 44 on top of waist elastics 68, 70, absorbent mediums 48 and the continuous supply of outer cover 46. Folding bars 09 then fold outer cover 46, which has a width greater than the width of absorbent medium 48 and bodyside liner 44, over mediums 48 and liner 44 to form baffles 62. After baffles 62 have been formed, supply rolls 110, 112 provide a continuous supply of elastic side panels 6, 8, and bonding station 114 then bonds, such as by ultrasonic, thermal, or adhesive bonding, elastic side panels 6, 8, bodyside liner 44 and outer cover 46. Leg cut-out station 116, which can be pressurized fluid-jets or a rotary die cutter, then cuts side panels 6, 8 to form intermediate portions 22. As the composite continues through the process, cutting station 118 severs the composite between waist elastics 68, 70, the composite is then tucked or folded in half by tucker bar 120, which contacts an intermediate portion of a severed composite and moves it between the individual conveyors of conveyor assembly 122. Located in conjunction with conveyor assembly 122 is seam bonding station 124 which bonds, such as by ultrasonic, thermal, or adhesive bonding, elastic side panels 6, 8 to form seams 28, 30 of absorbent garment 2. Conveyor assembly 122 then delivers absorbent garment 2 to transfer conveyor assembly 126, which delivers absorbent garments 2 to the next handling station.

The process illustrated in FIG. 14 can be easily adapted to make other embodiments such as those illustrated in FIG. 5A and FIG. 18, and other constructions such as those illustrated in FIGS. 8-10.

While this invention has been described as having preferred embodiments, it will be understood that it is capable of further modifications. This application is therefore intended to cover any variations, uses or adaptations of the invention following the general principles thereof, and including such departures from the present disclosure as come within known or customary practice in the art to which this invention pertains and fall within the limits of the appended claims.

What is claimed is:

1. A disposable pant-like garment for absorbing human discharge, comprising:

an absorbent assembly comprising a liquid impervious outer cover, a liquid pervious liner, and an absorbent medium therebetween, said absorbent assembly further comprising generally opposite side edges and generally opposite end edges, stretchable side panels and said absorbent assembly being joined to form a waist opening and a pair of leg openings, said absorbent assembly end edges being generally adjacent said waist opening, and a narrow intermediate portion of each said stretchable side panel being arranged generally adjacent a portion of a respective one of said leg openings, whereby said stretchable side panels provide generally inwardly directed force vectors against a wearer to maintain said garment snugly against the wearer's body and said absorbent assembly snugly in place against the crotch area both before and after a discharge, and said stretchable side panels provide elasticity about said leg openings to prevent leakage thereat.

2. A disposable pant-like garment for absorbing human discharge, comprising:

an absorbent assembly comprising a liquid impervious outer cover, a liquid pervious liner, and an absorbent medium therebetween, said absorbent assembly further comprising generally opposite side edges and generally opposite end edges, and stretchable side panels being joined to said side edges of said absorbent assembly to form with said absorbent assembly end edges a waist opening, stretchable side panels forming a pair of leg openings, whereby said stretchable side panels provide generally inwardly directed force vectors against a wearer to maintain said garment snugly against the wearer's body and said absorbent assembly snugly in place against the crotch area both before and after a discharge, and said stretchable side panels provide elasticity about said leg openings to prevent leakage thereat.

3. A disposable plant-like garment for absorbing human discharge, comprising:

an absorbent assembly comprising a liquid impervious outer cover, a liquid pervious liner, and an absorbent medium therebetween, said absorbent assembly further comprising generally opposite side edges and generally opposite end edges, stretchable side panels being joined to said side edges to form with said absorbent assembly a waist opening and a pair of leg openings, and a narrow intermediate portion of said stretchable side panels being arranged generally adjacent a portion of a respective one of said leg openings.

4. A disposable pant-like garment for absorbing human discharge, comprising:

an absorbent assembly comprising an outer cover and an absorbent medium, said absorbent assembly further comprising generally opposite side edges and generally opposite end edges, stretchable side panels being joined to said side edges to form with said absorbent assembly a waist opening and a pair of leg openings, and a narrow intermediate portion of said stretchable side panels being arranged generally adjacent a crotch portion of a respective one of said leg openings.

5. A disposable child's training pant comprising:

an absorbent assembly comprising an outer cover and an absorbent medium, said absorbent assembly further comprising generally opposite side edges and generally opposite end edges.

stretchable side panels being joined to said side edges to form with said absorbent assembly a waist opening and a pair of leg openings, and a narrow intermediate portion of said stretchable side panels being arranged generally adjacent a portion of a respective one of said leg openings 6. The garment of claim 1, 2 or 3 wherein an edge portion of each said side panel is joined between respective side portions of said outer cover and said liner.

7. The garment of claim 1, 3, 4, 5 wherein edge portions of said stretchable side panels directly abut against respective sides of said absorbent medium.

8. The garment of Claim 6 wherein said edge portions are spaced apart from respective sides of said absorbent medium from about 0 inches to about 2 inches.

9. The garment of Claim 8 wherein said edge portions are spaced apart from said sides from about 0 inches to about 1 inch.

10. The garment of Claim 9 wherein said edge portions are spaced apart from said sides from about 0 inches to about ½ inch.

11. The garment of Claim 1 wherein each said side panel extends over a respective side of said absorbent medium a distance of about 0% to about 50% of the maximum width of said absorbent medium.

12. The garment of claim 11 wherein each said side panel extends over a respective said side a distance of about 3% to about 20% of the maximum width of said absorbent medium.

13. The garment of claim 12 wherein each said side panel extends over a respective said side a distance of about 6% to about 12% of the maximum width of said absorbent medium.

14. The garment of claim 1 wherein said outer cover comprises at least two layers, the outermost one of said layers being made of a cloth-like material and the innermost one of said layers being made of a liquid-impervious material.

15. The garment of claim 14 wherein said outermost layer is a spunbonded thermoplastic material.

16. The garment of claim 14 wherein said outermost layer is a bonded carded web of thermoplastic material.

17. The garment of claim 14 wherein said innermost layer is a liquid impervious meltblown thermoplastic material.

18. The garment of claim 14 wherein said innermost layer is an extruded film of thermoplastic material.

19. The garment of claim 1 or 55 wherein each said side panel is stretch-bonded laminate comprising a stretchable layer stretch-bonded to a gatherable layer, whereby upon relaxing said stretch-bonded layers, said gatherable layer is gathered.

20. The garment of claim 19 wherein said stretch-bonded laminate comprises a second gatherable layer, said stretchable layer being stretch-bonded to said second gatherable layer, whereby upon relaxing said stretch-bonded layers, said second gatherable layer is gathered.

21. The garment of claim 1, 2, 3, 4, or 5 wherein at least one seam is manually tearable.

22. The garment of claim 1, 2, 3, 4 or 5 wherein each said side panel has a tension range per inch of about 50 grams to about 1,000 grams.

23. The garment of claim 22 wherein each said side panel has a tension range per inch of about 200 grams to about 500 grams.

24. The garment of claim 1, 2, 3, 4 or 5 wherein each said side panel has an elasticity of about 10% to about 500%.

25. The garment of claim 24 wherein each said side panel has an elasticity of about 50% to about 300%.

26. The garment of claim 25 wherein each said side panel has an elasticity of about 75% to about 200%.

27. The garment of claim 1, 2, 3, 4 or 5 further comprising a waist elastic at each end portion of said absorbent assembly.

28. The garment of claim 27 wherein said waist elastic is an energy activatable elastic material.

29. The garment of claim 27 wherein each said waist elastic comprises a plurality of elastic members.

30. The garment of claim 1, 3, 4 or 5 further comprising an elongate stretchable member disposed with a respective said intermediate portion to increase the elasticity thereof.

31. A disposable pant-like garment for absorbing human discharge, comprising:
   an absorbent assembly comprising a liquid impervious outer cover, a liquid pervious liner, and an absorbent medium therebetween, said absorbent assembly further comprising generally opposite side edges and generally opposite end edges,
   stretchable side panels and said absorbent assembly being joined to form a waist opening and a pair of leg openings, said absorbent assembly end edges being generally adjacent said waist opening,
   an intermediate portion of said stretchable side panels being arranged generally adjacent a portion of a respective one of said leg openings, and
   an upper end segment portion of said stretchable side panels tapering inwardly and upwardly toward said waist opening, thereby to provide a better fit at the waist of the wearer, whereby said stretchable side panels provide generally inwardly directed force vectors against the wearer to maintain said garment snugly against the wearer and said absorbent assembly snugly in place against the crotch area both before and after a discharge, and said stretchable side panels provide elasticity about said leg opening to prevent leakage thereat.

32. The garment of claim 31 wherein the length of each said end segment portion is about 3% to about 40% of the total length of said garment.

33. The garment of claim 32 wherein the length of each said end segment portion is about 5% to about 25% of the total length of said garment.

34. The garment of claim 33 wherein the length of each said end segment portion is about 10% to about 15% of the total length of said garment.

35. The garment of claim 31 wherein each said end segment portion angles inwardly toward said waist opening at an angle between about 5° to about 55°.

36. The garment of claim 35 wherein each said end segment portion angles inwardly toward said waist opening between about 10° to about 40°.

37. The garment of claim 36 wherein each said end segment portion angles inwardly toward said waist opening between about 15° to about 30°.

38. The garment of claim 31 wherein the front edge portion of each said leg opening is nearer to said waist opening than the back edge portion.

39. The garment of claim 1, 31, 2, 3, 4, or 5 wherein said side panels comprise between about 20% to about 80% of the total surface area of said garment.

40. The garment of claim 39 wherein said side panels comprise between about 25% to about 50% of the total surface area of said garment.

41. The garment of claim 40 wherein said side panels comprise between about 35% to about 45% of the total surface area of said garment.

42. The garment of claim 31 or 2 wherein the width of each said intermediate portion is between about 5% to about 100% of the maximum width of its respective said side panel.

43. The garment of claim 42 wherein the width of each said intermediate portion is between about 20% to about 80% of the maximum width of its respective said side panel.

44. The garment of claim 43 herein the width of each said intermediate portion is between about 30% to about 50% of the maximum width of its respective said side panel.

45. The garment of claim 31 or 2 wherein an edge portion of each said side panel is joined between said outer cover and said liner.

46. The garment of claim 45 wherein said edge portion of each said side panel directly abuts against said absorbent medium.

47. The garment of claim 45 wherein said edge portion of each said side panel is spaced apart from said absorbent medium from about 0 inches to about 2 inches.

48. The garment of claim 47 wherein said edge portions are spaced apart from said absorbent medium from about 0 inches to about 1 inch.

49. The garment of claim 48 wherein said edge portions are spaced apart from said absorbent medium from about 0 inches to about ½ inch.

50. The garment of claim 31 or 2 wherein each said side panel extends over said absorbent medium a distance of about 0% to about 50% of the maximum width of said absorbent medium.

51. The garment of claim 50 wherein each said side panel extends over said absorbent medium a distance of about 3% to about 20% of the maximum width of said absorbent medium.

52. The garment of claim 51 wherein each said side panel extends over said absorbent medium a distance of about 6% to about 12% of the maximum width of said absorbent medium.

53. The garment of claim 31 or 2 wherein each said side panel is a stretch-bonded laminate comprising a stretchable layer stretch-bonded to a gatherable layer, whereby upon relaxing said stretch bonded layers, said gatherable layer is gathered.

54. The garment of claim 53 wherein said stretch-bonded laminate comprises a second gatherable layer, said stretchable layer being stretch-bonded to said second gatherable layer, whereby upon relaxing said stretch-bonded layers, said second gatherable layer is gathered.

55. The garment of claim 1 wherein the width of each said intermediate potion is between about 5% to about 100% of the maximum width of its respective said side panel.

56. The garment of claim 2 wherein the width of each said intermediate portion is between about 20% to about 80% of the maximum width of its respective said side panel.

57. The garment of claim 56 wherein the width of each said intermediate portion is between about 30% to about 50% of the maximum width of its respective said side panel.

58. The garment of claim 1 wherein said intermediate portions form respective gussets at said leg openings.

* * * * *

UNITED STATES PATENT AND TRADEMARK OFFICE
CERTIFICATE OF CORRECTION

PATENT NO. : 4,938,757

DATED : July 3, 1990

INVENTOR(S) : Paul T. Van Gompel; Jody D. Suprise; Leona G. Boland; Georgia L. Zehner It is certified that error appears in the above-identified patent and that said Letters Patent is hereby corrected as shown below:

Column 2, line 50, add the number "1" before the word "in".

Column 2, line 56, delete the word "FIG." at the end of the line.

Column 5, line 10, delete the hyphen after the word "material" and substitute therefor --,--.

Column 9, line 12, add the word "cover" after the word "outer".

Column 12, line 29, delete the number "09" and insert therefor --109--.

Claim 2, column 13, line 32, add the word "said" before the word "stretchable".

Claim 7, column 14, line 12, add the word "or" before the number "5".

Claim 11, column 14, line 24, add ", 2, 3, 4, or 5" before the word "wherein".

Claim 14, column 14, line 36, add ", 2, 3, 4, or 5" before the word "wherein".

UNITED STATES PATENT AND TRADEMARK OFFICE
CERTIFICATE OF CORRECTION

PATENT NO. : 4,938,757
DATED : July 3, 1990
INVENTOR(S) : Paul T. Van Gompel; Jody D. Suprise; Leona G. Boland; Georgia L. Zehner It is certified that error appears in the above-indentified patent and that said Letters Patent is hereby corrected as shown below:

Claim 19, column 14, line 50, delete "or 55" and substitute therefor --, 2, 3, 4, or 5--.

Claim 55, column 16, line 55, add ", 2, 3, 4, or 5" before the word "wherein".

Claim 56, column 16, line 59, delete the number "2" and substitute therefor --55--.

Claim 58, column 16, line 66, add "3, 4, or 5" before the word "wherein".

Claim 3, Col. 13, line 41, "plant-like" should read --pant-like --.

Signed and Sealed this

Thirteenth Day of July, 1993

Attest:

MICHAEL K. KIRK

Attesting Officer     Acting Commissioner of Patents and Trademarks